Jan. 20, 1970 J. M. GARABEDIAN Plant Pat. 2,963
PEACH TREE
Filed June 26, 1968
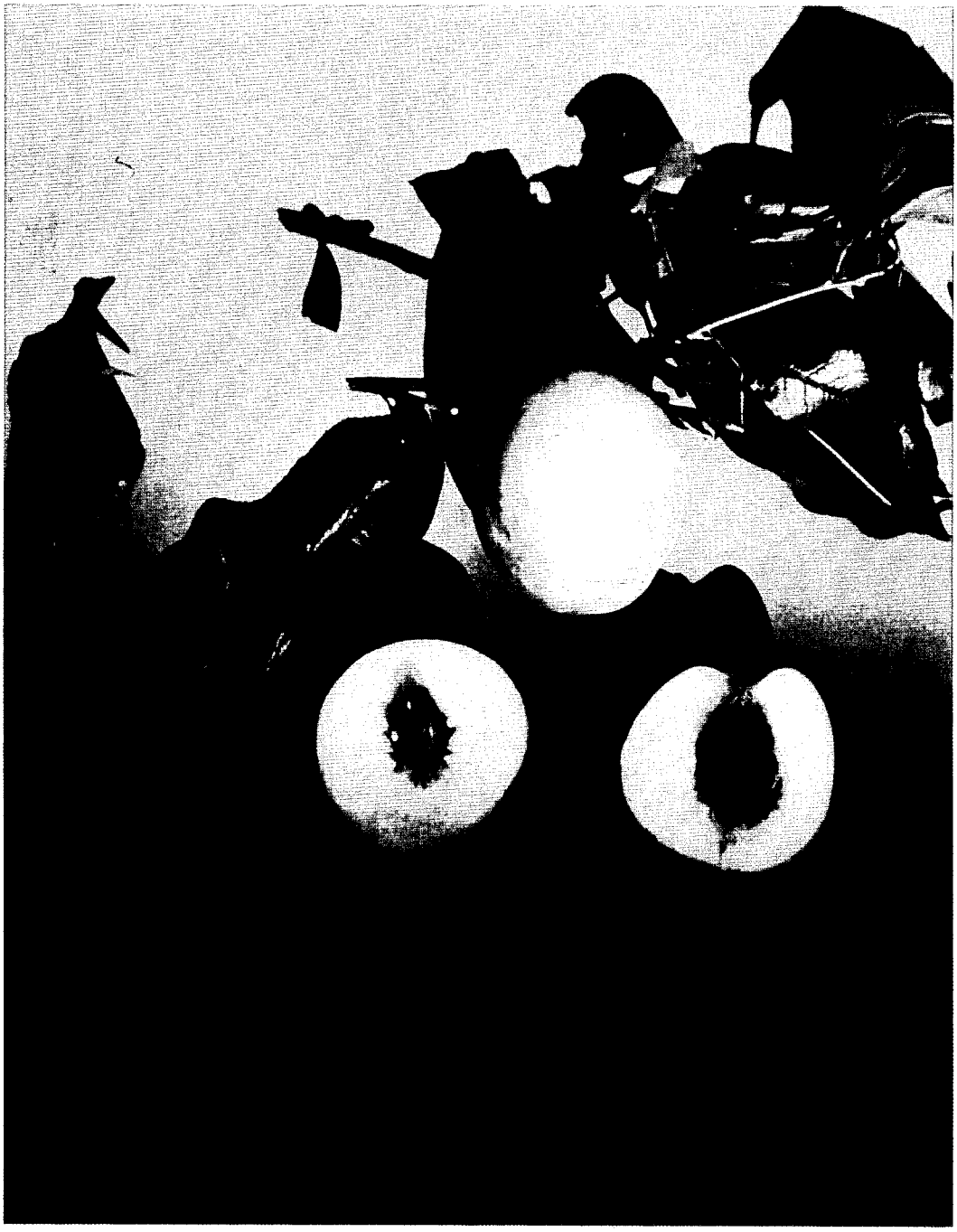
INVENTOR
John M. Garabedian
BY
Webster & Webster
ATTORNEYS United States Patent Office Plant Pat. 2,963
Patented Jan. 20, 1970

2,963
PEACH TREE

John M. Garabedian, Fresno, Calif., assignor to Peach & Willow Farms, Fresno, Calif., a corporation of California Filed June 26, 1968, Ser. No. 740,401
Int. Cl. A01h 5/08
U.S. Cl. Plt.—43 1 Claim

ABSTRACT OF THE DISCLOSURE

A variety of peach tree which is large in size, vigorous in growth, and a regular and productive bearer of large freestone fruit having yellow flesh, and yellow skin partially overspread with red.

ORIGIN OF THE VARIETY

Seeds from trees of the John G. (United States Plant Patent No. 1,141) peach were started in a hothouse and the resultant seedlings, subsequently planted on my ranch located near Fresno, Fresno County, California. Such seedlings were—under conditions of careful and continuing observation by me—grown and open pollinated to the point of bearing fruit. In comparison with each other, as well as with other known varieties, including the John G peach the fruit of one such seedling evidenced novel and commercially desirable characteristics. I, therefore, selected such one seedling—which is the instant variety—for asexual reproduction preparatory to introduction to the trade.

ASEXUAL REPRODUCTION OF THE VARIETY

The variety, originated in the manner described above, was asexually reproduced by me by budding on mature trees of the Richard Grand (United States Patent No. 2,419) nectarine; such budding having been accomplished in an orchard on my ranch located near Madera, Madera County, Calif. All such asexual reproductions were, in maturity, found to be quite true to the original tree in all respects.

SUMMARY OF THE VARIETY

The herein claimed variety of peach tree is hardy, large in size, vigorous in its spreading and open growth, vase-shaped, and a regular and productive bearer of large freestone fruit having yellow flesh, and yellow skin partially overspread with red, the latter being slightly mottled and streaked; the variety being particularly characterized, as to novelty, by an early September ripening period of highly colored, very tasty fruit which remains quite firm for shipping.

The present variety of peach tree is, more particularly, characterized by fruit having a ripening period which usually initiates early in the first week of September, and which is about one week to ten days later than the ripening period of the Rio Oso Gem (United States Plant Patent No. 84), but before the Kirkman Gem (United States Plant Patent No. 506), under like growing conditions.

The instant variety remains in harvest for about one week or a few days longer.

BRIEF DESCRIPTION OF THE DRAWING

The drawing is an illustration, by photographic reproduction in color, of fruit of the variety together with twigs and leaves; one of the fruit in the view being half cut away along the suture plane and another fruit being half cut away at a right angle to the suture plane, the stone remaining in the illustrated half of each cut fruit.

DESCRIPTION OF THE VARIETY

The botanical details of this new and distinct variety of peach tree—with color definitions (except those in common color terms) reference to Maerz and Paul Dictionary of Color—are as follows:

Tree:
- *Size.*—Large.
- *Vigor.*—Vigorous.
- *Growth.*—Spreading.
- *Density.*—Open.
- *Form.*—Vase-shaped.
- *Hardiness.*—Hardy.
- *Production.*—Productive.
- *Bearing.*—Regular.

Trunk:
- *Size.*—Medium.
- *Texture.*—Medium.

Branches:
- *Size.*—Stocky to medium.
- *Texture.*—Smooth.
- *Color.*—Current season's growth: ventral side—Absinthe Green (20–J–5); dorsal side—Wineberry Red (55–J–7). One-year wood.—Chestnut Brown (7–E–10).
- *Lenticels.*—Number—Numerous. Size—Medium.

Leaves:
- *Size.*—Large to medium—mostly large. Length—4¾″ to 7″, average 6¼″. Width—½″ to 1 9/16″, average 1½″.
- *Form.*—Lanceolate.
- *Thickness.*—Medium.
- *Texture.*—Smooth; glabrous; some slightly crinkled.
- *Leaf apex.*—Acutely pointed—mostly acuminate.
- *Leaf base.*—Mostly acute—some broadly acute.
- *Leaf veins.*—Pinnately net veined.
- *Margin.*—Glandular; crenate.
- *Petiole.*—Length—medium, ⅜″ to 9/16″, usually 9/16″. Thickness—medium, usually 1/16″ in diameter. Color: dorsal side—Fern Green (21–L–7); ventral side—Grape Green (21–J–1).
- *Glands.*—Average number—1 to 5, usually 2. Opposite to alternate, mostly opposite. Large to medium. usually large. Reniform; red. Positioned usually on petiole, some on base of leaf blade.
- *Stipules.*—Large on vigorous shoot; none to 2.
- *Leaf buds.*—Small; pointed.
- *Leaf color.*—Dorsal side—Mt. Vernon Green (23–J–8). Ventral side—Spinach Green (22–K–7).

Flower buds:
- *Hardiness.*—Hardy.
- *Size.*—Large to medium.
- *Length.*—Medium.
- *Form.*—Plump; free.
- *Pubescence.*—Pubescent.

Flowers:
- *Blooming period.*—Date of first bloom—Feb. 22, 1968. Date of full bloom—Mar. 1, 1968. Early to medium, as compared with other varieties.
- *Size.*—Large to medium.
- *Calyx diameter.*—Very large.
- *Sepal length.*—Medium to long.
- *Sepal width.*—Broad.
- *Pedicel length.*—Medium.
- *Petals.*—Large; showy; round.
- *Color.*—Pink (49–E–3) shading to light Valencia Pink (49–H–2).

Fruit:

*Maturity when described.*—Hard—minimum harvesting maturity.

*Date of first picking.*—Early part of the first week of September in normal season.

*Duration of picking.*—Approximately one week to ten days.

*Size.*—Uniform; large. Diameter axially—2½" to 3", average 2¾". Transversely in suture plane—2⅝" to 3¼", average 2⅞".

*Form.*—Uniform; unsymmetrical; round ovate. Transversely through diameter—some obovate, few slightly compressed on dorsal side.

*Suture.*—A distinct line with slight depression beyond pistil points, and some slight cleft in suture plane near base.

*Ventral surface.*—Rounded slightly—few rounded strongly.

*Lips.*—Lipped toward base—usually unequal.

*Cavity.*—Elongated in suture plane, with suture showing on one side. Average depth—½". Average breadth—¾". Average length—1". Color—Straw Yellow (10–F–2).

*Base.*—Truncate.

*Apex.*—Short; rounded; slightly depressed.

*Pistil point.*—Apical.

*Stem.*—Large; thick. Average length—⅜". Average width—⅛".

Skin:

*Thickness.*—Thick.

*Texture.*—Tough.

*Flavor.*—Mildly astringent.

*Tenacity.*—Tenacious to flesh.

*Tendency to crack.*—None in dry season.

*Pubescence.*—Moderate; short; does not roll up when rubbed.

*Color.*—Yellow, partially overspread with Dianthus Red (5–I–3), slightly mottled and sometimes slightly streaked with Zanzibar Red (8–L–5).

Flesh:

*Amygdalin.*—Wanting.

*Juice.*—Moderate; rich.

*Texture.*—Firm; fine; crisp to melting.

*Fibers.*—Few; fine; tender.

*Ripens.*—Evenly—earliest at apex.

*Flavor.*—Delicate to vinous.

*Aroma.*—Wanting.

*Eating quality.*—Very good.

*Color.*—Golden Corn Yellow (9–J–6) with reddish tinge toward apex. Slightly reddish specks in flesh near skin. Surface of pit cavity—Persian Pink (3–I–4), with white dots.

Stone:

*Type.*—Free—adheres to flesh along ventral edges ear stem end. Short fibers. Parts from flesh smoothly.

*Size.*—Medium—some large. Length—1⅜" to 1⅝", average 1½". Breadth—15/16" to 1⅛", average 1". Thickness—⅝" to ¾", average 11/16".

*Form.*—Obovoid.

*Base.*—Straight.

*Hilum.*—Oval to oblong—mostly narrow.

*Apex.*—Rounded.

*Sides.*—Equal.

*Surface.*—Irregularly furrowed near base toward ventral edge; ridged near apex; pitted toward base.

*Ridges.*—On either side; interrupted; jagged toward base and apex.

*Pits.*—Circular to elongated.

*Ventral edge.*—Thick, without wing throughout.

*Dorsal edge.*—Narrow, with shallow narrow groove toward base.

*Thickness of pit wall.*—⅛" to 3/16".

*Tendency to slit.*—None in dry season.

*Kernel.*—Ovate—elongated. Slightly bitter almond flavor. Usually viable. Average width—7/16". Average length—13/16". Pellicle color—Cacao Brown (5–A–11). Moderate amygdalin.

*Color.*—Formosa Brown (12–D–8) at base end to Hazel Brown (13–J–9) at middle of stone.

Use: Market; dessert; culinary.

Keeping quality: Good.

Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is hardly, large in size, vigorous in its spreading and open growth, vase-shaped, and a regular and productive bearer of large freestone fruit having yellow flesh and yellow skin partially overspread with red, the latter being slightly mottled and streaked; characterized by the fruit being highly colored, very tasty, and normally ripening about a week to ten days later than the Rio Oso Gem under like growing conditions.

No references cited.

ROBERT E. BAGWILL, Primary Examiner